United States Patent [19]

Haller

[11] Patent Number: 4,692,156

[45] Date of Patent: Sep. 8, 1987

[54] DISPOSABLE SYRINGE WITH RETRACTABLE CANNULA

[76] Inventor: Irene Haller, 7981 Stonehurst Ct., Pleasanton, Calif. 94566

[21] Appl. No.: 851,532

[22] Filed: Apr. 14, 1986

Related U.S. Application Data

[63] Continuation-in-part of Ser. No. 806,100, Dec. 6, 1985, abandoned.

[51] Int. Cl.$^4$ .............................................. A61M 5/32
[52] U.S. Cl. .................................... 604/195; 128/763
[58] Field of Search .............. 604/195, 196, 197, 198, 604/218; 128/763, 764, 765

[56] References Cited

U.S. PATENT DOCUMENTS 3,930,492  1/1976  Hatsuno et al. .................... 128/765

Primary Examiner—John D. Yasko
Attorney, Agent, or Firm—Majestic, Gallagher, Parsons & Siebert

[57] ABSTRACT

An improved hypodermic syringe having a cannula retractable within the syringe barrel after injection. A piston in reciprocable sealing engagement with the interior of the syringe barrel includes an engaging structure at its forward end which is attachable to the cannula base. After administration of the fluid contained within the syringe chamber, the piston engages the cannula base, preferably by "snapping" on to the rearward end of the cannula, and retracts the cannula within the barrel. The barrel may additionally be designed so as to prevent complete removal of the piston. In an alternative embodiment, a cannula retracting mechanism is provided in a hypodermic syringe assembly for drawing blood.

11 Claims, 5 Drawing Figures

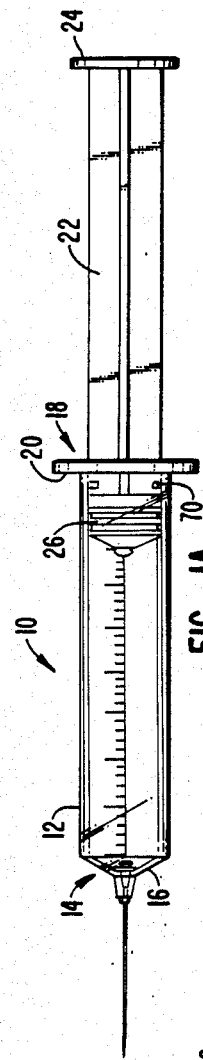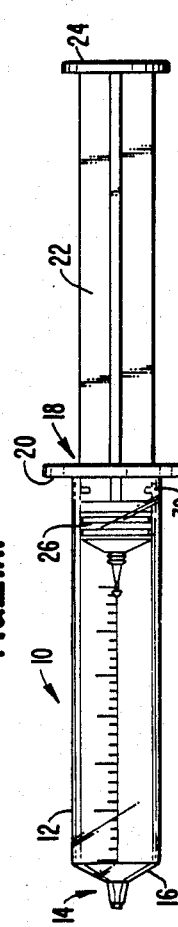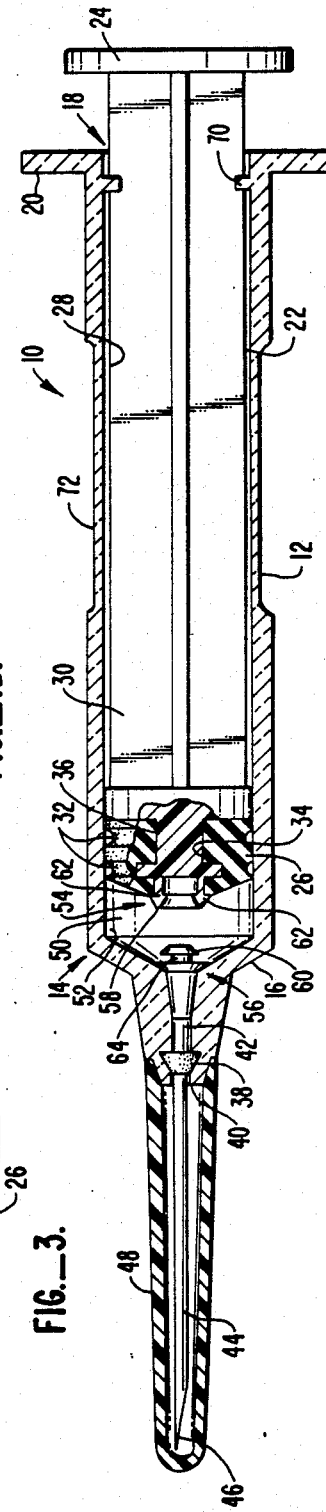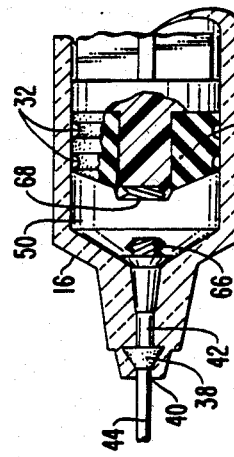

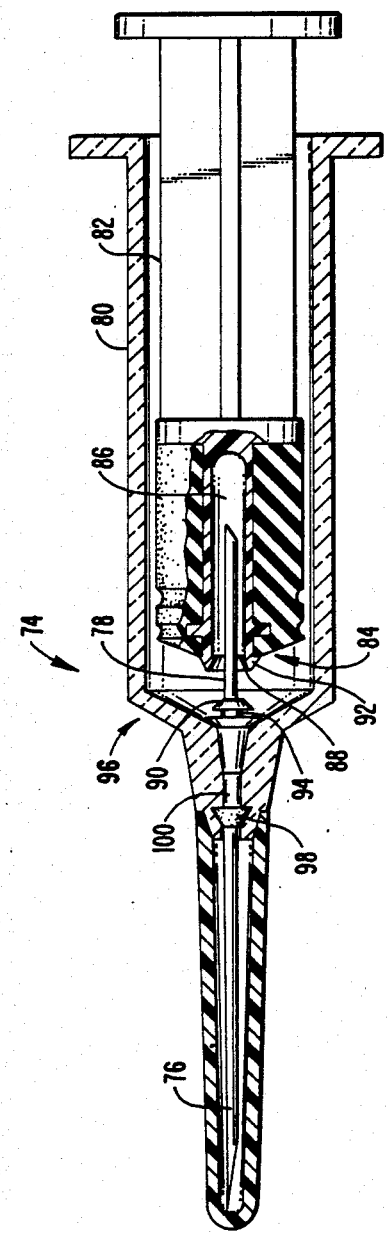
FIG._4.

DISPOSABLE SYRINGE WITH RETRACTABLE CANNULA

This is a continuation-in-part of U.S. patent application Ser. No. 806,100 filed Dec. 6, 1985 now abandoned in the name of inventor Irene Haller.

FIELD OF THE INVENTION

This invention relates generally to disposable syringes. In particular, the invention relates to a disposable hypodermic syringe which may be used in the administration of serum, antibiotics, or the like and in which the sharp-pointed cannula thereof is retractable subsequent to injection to avoid contamination and injury.

BACKGROUND OF THE INVENTION

Current hypodermic syringes present a problem in that the sharp-pointed cannulas thereof frequently cause injury and infection subsequent to administration of medicinal fluid. Typically, a hypodermic syringe is used in the form of a disposable, preloaded syringe of plastic material having a barrel and a piston reciprocable by means of a plunger therein. A sharp-pointed cannula is normally fixed to the forward wall of the syringe barrel and protected by means of a removable plastic sheath. U.S. Pat. No. 4,317,446 to Ambrosio et al., for example, shows such a syringe.

A serious problem presented by many prior art syringes results from exposure of the protruding cannula after use. The person administering the injection may inadvertently become stuck by the contaminated cannula. This not infrequent incidence of contamination can cause the spread of various diseases, including hepatitis and acquired immune deficiency syndrome (AIDS). In addition to the serious danger posed to health care workers, such accidents are costly to hospitals and other medical facilities in terms of time and administration costs; typically, an incident report has to be filled out for each such inadvertent wounding.

One solution to this problem has been to cover the cannula after use with a cap-like "Luer-locking" ("Luer-Lok" is a trademark of Becton-Dickinson Co., Rutherford, N.J.) structure (see, e.g., U.S. Pat. No. 4,540,405 to Miller et al.). However, the possibility of inadvertent piercing of one's finger after injection remains. It is thus desirable to provide an alternative design of syringe so as to safely and easily prevent exposure of the needle after injection. U.S. Pat. No. 4,026,287, of common inventorship herewith and over which the instant device is an improvement, provides a proposed solution. In that patent, the disclosure of which is hereby incorporated by reference in its entirety, I proposed a syringe having a breakable end wall at the forward end of the syringe barrel, the cannula mounted on the end wall and severable therefrom upon retraction of the piston. The instant invention, while directed toward the substantially identical problem, provides a syringe which is easier and less costly to manufacture, having fewer parts and being of generally simpler design.

SUMMARY OF THE INVENTION

Accordingly, it is an object of the present invention to provide an improved hypodermic syringe which substantially prevents injury and contamination after injection.

It is another object of the present invention to provide an improved hypodermic syringe having a cannula which is retractable entirely within the syringe barrel subsequent to discharge of fluid.

It is still another object of the present invention to provide an improved hypodermic syringe in which the forward end of the piston is engageable with the rearward end of the cannula, the engaging means on the piston being either a gripping means or a thread means.

It is yet another object of the present invention to provide an improved hypodermic syringe in which complete retraction of the piston therefrom is prevented.

It is a further object of the present invention to provide an improved hypodermic syringe in which complete retraction of the piston is prevented by means of a deformable section at a point between the forward and rearward ends of the syringe barrel, so that the barrel may be bent to prevent protrusion of the cannula tip after retraction.

It is still a further object of the present invention to provide an apparatus for drawing blood, the apparatus including a means for substantially preventing injury and contamination.

It is another object of the present invention to provide a hypodermic syringe assembly for drawing blood, the assembly having a cannula which is retractable entirely within the syringe barrel.

Additional objects, advantages and novel features of the invention will be set forth in part in the description which follows, and in part will become apparent to those skilled in the art on examination of the following, or may be learned by practice of the invention. The objects and advantages of the invention may be realized and attained by means of the instrumentalities and combinations particularly pointed out in the appended claims.

In one embodiment of the present invention, an improved hypodermic syringe is provided having a hollow, generally tubular barrel substantially closed at its forward end and open at its rearward end. A tubular reciprocable piston means is provided within the interior of the barrel, which piston means has a generally annular resilient rubber member at the forward end. A means for retracting the cannula, protruding from said barrel structure during injection, is provided on the forward end of the piston. The retracting means includes an engaging means on the forward end of the piston attachable to the base of the cannula. Thus, after injection, the cannula may be easily and safely withdrawn within the interior of the barrel.

In an alternative embodiment, the syringe is further provided with a means for limiting retraction of the piston from the barrel. This limiting means may be a section of deformable plastic at a point between the forward end and the rearward end of the barrel, so that the barrel may be bent after injection, preventing complete removal of the piston and resultant exposure of the cannula. Alternatively, the limiting means may be an annular ridge provided on the interior of the barrel adjacent its open end.

BRIEF DESCRIPTION OF THE DRAWINGS

FIG. 1A is a front elevational sectional view of a syringe of the instant invention shown prior to injection of the fluid contained therein.

FIG. 1B is a view of the same shown after injection of fluid has been completed and after retraction of the cannula.

FIG. 2 is a cross-sectional view of the syringe shown prior to retraction of the cannula, and illustrates a preferred embodiment of the invention.

FIG. 3 is a partial cross-sectional view of an alternative embodiment of the syringe, and illustrates a second means for retracting the cannula.

FIG. 4 is a partial cross-sectional view of a hypodermic syringe assembly for drawing blood, and illustrates the inventive mechanism for retracting the cannula of the assembly after blood has been drawn.

DETAILED DESCRIPTION OF THE INVENTION

In the drawings, the disposable syringe of the instant invention is shown generally at 10, comprising a generally tubular hollow barrel 12 of plastic material. The plastic is preferably transparent for viewing of the syringe contents. The barrel is substantially closed at its forward end 14 by end wall 16, while the rearward end of the barrel 18 is open. An annular rib 20 is provided around the open rearward end of the barrel to provide a place for gripping by the operator's fingers.

Projecting from the rearward end of the syringe barrel is a plunger rod 22 of generally cruciform shape in cross section and having a flat planar thumb surface 24 at the rearward end thereof. At the forward end of plunger rod 22 is mounted a resilient annular piston head 26 which is in reciprocable sealing engagement with the syringe barrel interior 28. Plunger rod 22, thumb surface 24, and annular piston head 26 together comprise piston means 30. The plunger rod is preferably made of plastic material with the annular piston head preferably of rubber material in order to ensure a secure vacuum seal. As seen in FIG. 2, annular piston head 26 has a pair of spaced annular sealing ridges 32 therearound, and a bore 34 therethrough so that the piston may be fitted within an accomodating recess 36 at the front end of plunger rod 22.

At the forward end of the syringe barrel is a deformable tapered mounting post 38 positioned within aperture 40 having a passage 42 axially positioned therein leading from end wall 16 to the exterior of the syringe. Within passage 42 is fixedly mounted a cannula 44 having a sharp-pointed tip 46 at its forward end. In order to guard against contamination of the cannula and accidental puncturing of the operator, a tapered hollow sheath 48 is fitted over cannula 44. This tapered hollow sheath may be removed prior to injection to expose the sharp-pointed cannula 42.

In operation, an injection is given to dispense fluid 50 from chamber 52 through the interior passage (not shown) of the cannula 22 upon advance of the plunger rod 22 towards the forward end of the syringe barrel. This invention is directed toward retraction of cannula 44 within the barrel 12 after administration of fluid so as to prevent cannula exposure after injection.

Retraction of the cannula is accomplished by retracting means 52, which generally comprises an engaging means 54 on the forward end of piston means 30 attachable to the rearward end 56 of the cannula, which rearward end protrudes within chamber 52; attachment is accomplished by means of mating surfaces on engaging means 54 and on rearward end 56 of the cannula. In a preferred embodiment of the invention, and as illustrated in FIG. 2, engaging means 54 is a gripping means 58, preferably of hard plastic material, which "snaps" onto cannula base 60 (also preferably of hard plastic) by means of protruding gripping member 62 which is structured so as to fit snugly into corresponding groove 64. Thus, after injection, gripping means 58 attaches onto cannula base 60 and retracts the cannula within the syringe barrel. During retraction, deformable mounting post 38 deforms and slides through passage 42 while gripping means 58 firmly holds cannula base 60. The forces tending to hold gripping member 62 within groove 64 are thus greater than forces tending to maintain cannula 44 in its original position. FIG. 1B illustrates the syringe after retraction.

In an alternative embodiment, illustrated in FIG. 3, cannula base 60 is provided with thread means 66 which engages in an accomodated threaded recess 68 in annular piston head 26. When the plunger rod is fully advanced after injection, it is rotated to engage rearward end 56 of cannula 44 and pulled back toward the rearward end of barrel 12 to retract cannula 44 within the barrel.

In a modified, essentially "reverse" version of this embodiment, the protruding thread means may be on annular piston head 26, while the threaded recess would correspondingly be in cannula base 60.

After retraction of the cannula within the syringe barrel, it is desirable to prevent complete removal of the piston means 30 from the barrel which would expose the cannula. Accordingly, an annular ridge 70 is provided extending radially inward from the interior of barrel 12, adjacent the open rearward 18 of the barrel. FIG. 1B illustrates that after retraction of the cannula, complete retraction of the piston means is not possible by virtue of annular ridge 70. As an alternative to annular ridge 70, barrel 12 may be provided with a thin-walled or otherwise deformable section 72 at a point between its forward and rearward ends, so that the operator may bend the entire syringe after injection and retraction of the cannula, thus preventing complete removal of the piston means after use or protrusion of the cannula. Protrusion of the cannula after retraction may also be prevented by structuring retraction means 52 so as to maintain the cannula at an angle relative to the long axis of plunger rod 22, i.e. causing the cannula to be "off-center" after retraction. If desired, deformation may be facilitated by means of at least one circumferential groove (not shown) provided in deformable section 72.

FIG. 4 illustrates a hypodermic syringe assembly 74 for drawing blood, which assembly incorporates the inventive retraction means outlined above. The assembly 74 is similar to that shown in FIG. 2. However, in addition to external cannula 76, the assembly is provided with an internal cannula 78 extending inward from the forward end 96 of syringe barrel 80. Plunger rod 82 is similar to the plunger rod (22) of FIG. 2; however, at its forward end 84 is a recess 86 adapted to accommodate internal cannula 78. After drawing blood, plunger rod 82 is inserted into syringe barrel 80 in order to retract external cannula 76. Gripping means 88 on the plunger rod 82 snaps onto cannula base 90 by means of protruding gripping member 92 which is structured so as to fit into corresponding groove 94; the plunger rod may then be retracted along with external cannula 76 while deformable mounting post 98 deforms and slides through passage 100, as in the syringe, assembly described above and illustrated in FIG. 2. Alternatively, the assembly may be provided with the threaded retraction means shown in FIG. 3.

While the invention has been described in conjunction with the preferred specific embodiments thereof, it will be understood that this description is intended to illustrate and not limit the scope of the invention which is defined by the following appended claims.

What is claimed is:

1. An improved hypodermic syringe, comprising:
   a hollow barrel substantially closed at a forward end and provided with an open rearward end;
   a piston means in reciprocable sealing engagement with the interior of said barrel, defining a chamber in said barrel for containing fluid;
   a cannula, the rearward end of which is mounted at the closed end of said barrel, the forward end of which protrudes from said barrel, said cannula having an interior passage; and
   an aperture at the forward end of said barrel communicating said cannula interior passage with said chamber, the improvement which comprises a means for retracting said cannula within said chamber, said retracting means including an engaging means at the forward end of said piston means attachable to the rearward end of said cannula, whereby subsequent to discharge of fluid from said chamber, said piston means engages and retracts said cannula, and wherein said barrel has a thin-walled section between its forward and rearward ends so that the barrel may be deformed after said cannula is retracted thereby preventing all subsequent protrusion of said cannula from said barrel or complete removal of said plunger from said barrel.

2. The invention of claim 1, wherein said engaging means and said rearward end of said cannula are provided with mating surfaces.

3. The invention of claim 2, wherein said engaging means comprises a gripping means adapted to secure the rearward end of said cannula.

4. The invention of claim 2, wherein said mating surfaces are in the form of thread means, so that turning of said piston subsequent to discharge of fluid from said chamber causes engagement or disengagement of said thread means.

5. The invention of claim 1, further including in said barrel a means for preventing complete removal of said piston means from said barrel.

6. The invention of claim 5, wherein said means for preventing removal comprises an annular ridge extending radially inward from said barrel, adjacent said open end of said barrel.

7. The invention of claim 1, further including at least one circumferential groove at a point in said thin-walled section between said forward end and said rearward end of said barrel.

8. The invention of claim 1 wherein said cannula has a sharp pointed end to facilitate puncture.

9. A mechanism for retracting the cannula of a hypodermic syringe assembly for drawing blood, comprising:
   a hollow barrel substantially closed at a forward end and provided with an open rearward end;
   an external cannula, the rearward end of which is mounted at the closed end of said barrel, the forward end of which protrudes from said barrel, said cannula having an interior passage;
   an aperture at the forward end of said barrel communicating said interior passage of said cannula with the interior of said barrel;
   a piston means insertable into said barrel through said open rearward end, said piston means being provided with a means for retracting said external cannula within the interior of said barrel after blood has been drawn, said retracting means including an engaging means at the forward end of said piston attachable to the rearward end of said external cannula, whereby subsequent to drawing of blood, said piston means engages and retracts said external cannula, and wherein said forward end of said piston means is provided with a recess for accommodating said internal cannula.

10. The invention of claim 9 wherein said engaging means comprises gripping means adapted to secure the rearward end of said cannula.

11. The invention of claim 9 wherein said engaging means comprise threads.

* * * * *